(12) United States Patent
Mates et al.

(10) Patent No.: US 12,090,155 B2
(45) Date of Patent: Sep. 17, 2024

(54) METHODS

(71) Applicant: INTRA-CELLULAR THERAPIES, INC., New York, NY (US)

(72) Inventors: Sharon Mates, New York, NY (US); Robert Davis, San Diego, CA (US); Kimberly Vanover, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 18/494,754

(22) Filed: Oct. 25, 2023

(65) Prior Publication Data

US 2024/0066030 A1    Feb. 29, 2024

Related U.S. Application Data

(63) Continuation of application No. 16/922,893, filed on Jul. 7, 2020.

(60) Provisional application No. 62/871,170, filed on Jul. 7, 2019.

(51) Int. Cl.
*A61K 31/4985* (2006.01)
*A61K 9/20* (2006.01)
*A61K 9/48* (2006.01)
*A61P 25/18* (2006.01)
*A61K 45/06* (2006.01)

(52) U.S. Cl.
CPC ............ *A61K 31/4985* (2013.01); *A61K 9/20* (2013.01); *A61K 9/48* (2013.01); *A61P 25/18* (2018.01); *A61K 45/06* (2013.01)

(58) Field of Classification Search
CPC ................. A61K 31/5383; A61K 31/4985
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,001,263 A | 1/1977 | Plattner et al. |
| 4,115,577 A | 9/1978 | Rajagopalan |
| 4,136,145 A | 1/1979 | Fuchs et al. |
| 4,183,936 A | 1/1980 | Rajagopalan |
| 4,219,550 A | 8/1980 | Rajagopalan |
| 4,238,607 A | 12/1980 | Rajagopalan |
| 4,389,330 A | 6/1983 | Tice et al. |
| 4,522,944 A | 6/1985 | Doria et al. |
| 4,530,840 A | 7/1985 | Tice et al. |
| 4,767,628 A | 8/1988 | Hutchinson |
| 4,849,246 A | 7/1989 | Schmidt |
| 4,971,971 A | 11/1990 | Tokunaga et al. |
| 4,985,432 A | 1/1991 | Tokunaga et al. |
| 5,004,602 A | 4/1991 | Hutchinson |
| 5,114,976 A | 5/1992 | Norden |
| 5,151,419 A | 9/1992 | Perenyi et al. |
| 5,538,739 A | 7/1996 | Bodmer et al. |
| 5,648,539 A | 7/1997 | Goodbrand |
| 5,648,542 A | 7/1997 | Goodbrand et al. |
| 5,654,482 A | 8/1997 | Goodbrand |
| 5,688,801 A | 11/1997 | Mesens et al. |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,763,476 A | 6/1998 | Delbressine et al. |
| 5,779,231 A | 6/1998 | Mesens et al. |
| 5,834,493 A | 11/1998 | Gil Quintero et al. |
| 5,902,901 A | 5/1999 | Goodbrand et al. |
| 5,922,338 A | 7/1999 | Brich et al. |
| 5,922,682 A | 7/1999 | Brich et al. |
| 5,948,430 A | 9/1999 | Zerbe et al. |
| 5,965,168 A | 10/1999 | Mesens et al. |
| 6,043,370 A | 3/2000 | Kubo et al. |
| 6,110,921 A | 8/2000 | Mesens et al. |
| 6,323,366 B1 | 11/2001 | Wolfe et al. |
| 6,368,632 B1 | 4/2002 | Mesens et al. |
| 6,407,092 B1 | 6/2002 | Hester et al. |
| 6,419,952 B2 | 7/2002 | Wong et al. |
| 6,541,639 B2 | 4/2003 | Zhou et al. |
| 6,544,559 B2 | 4/2003 | Mesens et al. |
| 6,548,493 B1 | 4/2003 | Robichaud et al. |
| 6,552,017 B1 | 4/2003 | Robichaud et al. |
| 6,579,881 B2 | 6/2003 | Kitazawa et al. |
| 6,699,852 B2 | 3/2004 | Robichaud et al. |
| 6,713,471 B1 | 3/2004 | Robichaud et al. |

(Continued)

FOREIGN PATENT DOCUMENTS

GB      1476087     6/1977
WO   WO 1995/026325   10/1995

(Continued)

OTHER PUBLICATIONS

"Clinical Trial Evaluating ITI-007 as an Adjunctive Therapy to Lithium or Valproate for the Treatment of Bipolar Depression," ClinicalTrials.gov, 6 pages, Nov. 9, 2015.
Intra-Cellular Therapies, Inc., "Corporate Presentation" (Sep. 24, 2019), downloaded from https://ir.intracellulartherapies.com/static-files/93b08960-f01c-4864-aa22-8cadb3539753 (last accessed Mar. 13, 2023).
"Study of a Novel Antipsychotic ITI-007 in Schizophrenia," Clinical Trials.gov, 6 pages, Dec. 26, 2011.
Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.
Angst et al. "Prevalence and Characteristics of Undiagnosed Bipolar Disorders in Patients With a Major Depressive Episode", Arch Gen Psychiatry, vol. 68(8), p. 701-709, (2011).

(Continued)

*Primary Examiner* — Rei Tsang Shiao
(74) *Attorney, Agent, or Firm* — Hoxie & Associates LLC

(57) ABSTRACT

The disclosure provides methods for the treatment of Bipolar II Disorder, comprising administering to a patient in need thereof, a therapeutically effective amount of lumateperone, in free or pharmaceutically acceptable salt form, optionally in deuterated form.

27 Claims, No Drawings

(56) References Cited

U.S. PATENT DOCUMENTS

| | | |
|---|---|---|
| 6,762,329 B2 | 7/2004 | Marcoux et al. |
| 6,803,055 B2 | 10/2004 | Mesens et al. |
| 6,849,619 B2 | 2/2005 | Robichaud et al. |
| 6,849,640 B2 | 2/2005 | Ennis et al. |
| 6,884,429 B2 | 4/2005 | Koziak et al. |
| 6,929,803 B2 | 8/2005 | Wong et al. |
| 7,071,186 B2 | 7/2006 | Robichaud et al. |
| 7,071,201 B2 | 7/2006 | Kitazawa et al. |
| 7,081,455 B2 | 7/2006 | Robichaud et al. |
| 7,109,339 B2 | 9/2006 | Lee et al. |
| 7,118,763 B2 | 10/2006 | Mesens et al. |
| 7,183,282 B2 | 2/2007 | Robichaud et al. |
| 7,223,870 B2 | 5/2007 | Ghosh et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,244,734 B2 | 7/2007 | Iwema Bakker et al. |
| 7,375,226 B2 | 5/2008 | Jolidon et al. |
| 7,462,641 B2 | 12/2008 | Igo et al. |
| 7,547,452 B2 | 6/2009 | Mesens et al. |
| 7,592,454 B2 | 9/2009 | Lee et al. |
| 7,598,273 B2 | 10/2009 | Gant et al. |
| 7,601,740 B2 | 10/2009 | Weiner et al. |
| 7,614,727 B2 | 11/2009 | Hori |
| 7,645,752 B2 | 1/2010 | McDevitt et al. |
| 7,659,285 B2 | 2/2010 | Weiner et al. |
| 7,713,995 B2 | 5/2010 | Weiner et al. |
| 7,732,462 B2 | 6/2010 | Weiner et al. |
| 7,750,168 B2 | 7/2010 | Potyen et al. |
| 7,968,538 B2 | 6/2011 | Becker et al. |
| 7,994,193 B2 | 8/2011 | Weiner et al. |
| 7,998,971 B2 | 8/2011 | Barlow et al. |
| 8,008,323 B2 | 8/2011 | Weiner et al. |
| 8,227,487 B2 | 7/2012 | Weiner et al. |
| 8,309,722 B2 | 11/2012 | Tomesch et al. |
| 8,377,959 B2 | 2/2013 | Weiner et al. |
| 8,414,922 B2 | 4/2013 | Bryson et al. |
| 8,461,148 B2 | 6/2013 | Hollander |
| 8,475,793 B2 | 7/2013 | De Waal Malefyt et al. |
| 8,598,119 B2 | 12/2013 | Mates et al. |
| 8,604,021 B2 | 12/2013 | Becker et al. |
| 8,618,130 B2 | 12/2013 | Weiner et al. |
| 8,648,077 B2 | 2/2014 | Tomesch et al. |
| 8,697,700 B2 | 4/2014 | Surman et al. |
| 8,779,139 B2 | 7/2014 | Tomesch et al. |
| 8,791,138 B2 | 7/2014 | Seeman et al. |
| 8,921,393 B2 | 12/2014 | Weiner et al. |
| 8,993,572 B2 | 3/2015 | Mates et al. |
| 9,108,340 B2 | 8/2015 | Yang et al. |
| 9,168,258 B2 | 10/2015 | Mates et al. |
| 9,199,995 B2 | 12/2015 | Tomesch et al. |
| 9,211,289 B2 | 12/2015 | Weiner et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,428,506 B2 | 8/2016 | Mates et al. |
| 9,566,271 B2 | 2/2017 | Weiner et al. |
| 9,567,327 B2 | 2/2017 | Xiong et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,028,944 B2 | 7/2018 | Weiner et al. |
| 10,072,010 B2 | 9/2018 | Li et al. |
| 10,077,267 B2 | 9/2018 | Mates et al. |
| 10,117,867 B2 | 11/2018 | Mates et al. |
| 10,179,776 B2 | 1/2019 | Davis et al. |
| 10,221,176 B2 | 3/2019 | Tomesch et al. |
| 10,245,260 B2 | 4/2019 | Yao et al. |
| 10,322,134 B2 | 6/2019 | Vanover et al. |
| 10,464,938 B2 | 11/2019 | Tomesch et al. |
| 10,472,359 B2 | 11/2019 | Li et al. |
| 10,525,046 B2 | 1/2020 | Weiner et al. |
| 10,597,394 B2 | 3/2020 | Mates et al. |
| 10,597,395 B2 | 3/2020 | Tomesch et al. |
| 10,654,854 B2 | 5/2020 | Li et al. |
| 10,688,097 B2 | 6/2020 | Yao et al. |
| 10,702,522 B2 | 7/2020 | Mates et al. |
| 10,716,786 B2 | 7/2020 | Li et al. |
| 10,799,500 B2 | 10/2020 | Yao et al. |
| 10,844,061 B2 | 11/2020 | Li et al. |
| 10,899,762 B2 | 1/2021 | Tomesch et al. |
| 10,906,906 B2 | 2/2021 | Li et al. |
| 10,960,009 B2 | 3/2021 | Vanover et al. |
| 10,960,010 B2 | 3/2021 | Vanover et al. |
| 10,961,245 B2 | 3/2021 | Li et al. |
| 11,014,925 B2 | 5/2021 | Li et al. |
| 11,026,951 B2 * | 6/2021 | Vanover .................. A61P 25/24 |
| 11,052,083 B2 | 7/2021 | Mates et al. |
| 11,053,245 B2 | 7/2021 | Mates et al. |
| 11,096,944 B2 | 8/2021 | Yao et al. |
| 11,124,514 B2 | 9/2021 | Mates et al. |
| RE48,839 E | 12/2021 | Mates et al. |
| 11,311,536 B2 | 4/2022 | Li et al. |
| 11,331,316 B2 | 5/2022 | Li et al. |
| 11,376,249 B2 | 7/2022 | Li et al. |
| 11,427,587 B2 | 8/2022 | Li et al. |
| 11,723,909 B2 | 8/2023 | Yao et al. |
| 11,806,347 B2 | 11/2023 | Li et al. |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2004/0186136 A1 | 9/2004 | Alken et al. |
| 2005/0166771 A1 | 8/2005 | Gygi et al. |
| 2005/0182749 A1 | 8/2005 | Matsui |
| 2005/0222209 A1 | 10/2005 | Zeldis et al. |
| 2005/0222238 A1 | 10/2005 | Alken |
| 2006/0178362 A1 | 8/2006 | Robichaud et al. |
| 2006/0205787 A1 | 9/2006 | Muller et al. |
| 2008/0069885 A1 | 3/2008 | Mesens et al. |
| 2008/0132552 A1 | 6/2008 | Kleinman et al. |
| 2008/0280941 A1 | 11/2008 | Lourtie |
| 2009/0076159 A1 | 3/2009 | Czarnik |
| 2010/0159033 A1 | 6/2010 | Gant et al. |
| 2011/0269777 A1 | 11/2011 | Bachurin et al. |
| 2014/0080816 A1 | 3/2014 | Koolman et al. |
| 2015/0072964 A1 | 3/2015 | Mates et al. |
| 2016/0310502 A1 * | 10/2016 | Vanover .................. A61P 25/24 |
| 2016/0354315 A1 | 12/2016 | Li |
| 2017/0114037 A1 | 4/2017 | Davis et al. |
| 2017/0183350 A1 | 6/2017 | Mates et al. |
| 2019/0071445 A1 | 3/2019 | Li et al. |
| 2019/0183888 A1 | 6/2019 | Mates et al. |
| 2019/0192511 A1 | 6/2019 | Li et al. |
| 2019/0211015 A1 | 7/2019 | Mittleman et al. |
| 2019/0231780 A1 | 8/2019 | Yao et al. |
| 2019/0328745 A1 | 10/2019 | Vanover et al. |
| 2019/0388418 A1 | 12/2019 | Li et al. |
| 2020/0087305 A1 | 3/2020 | Tomesch et al. |
| 2020/0102304 A1 | 4/2020 | Li et al. |
| 2020/0157100 A1 * | 5/2020 | Li ............................ A61P 25/18 |
| 2020/0392135 A1 | 12/2020 | Wennogle et al. |
| 2020/0405713 A1 | 12/2020 | Mates et al. |
| 2020/0407362 A1 | 12/2020 | Mates et al. |
| 2021/0002280 A1 | 1/2021 | Mates et al. |
| 2021/0008065 A1 | 1/2021 | Li et al. |
| 2021/0009592 A1 | 1/2021 | Li et al. |
| 2021/0032247 A1 | 2/2021 | Li et al. |
| 2021/0060009 A1 | 3/2021 | Snyder et al. |
| 2021/0093634 A1 | 4/2021 | Snyder et al. |
| 2021/0145829 A1 | 5/2021 | Li et al. |
| 2021/0163481 A1 | 6/2021 | Li et al. |
| 2021/0315891 A1 | 10/2021 | Li et al. |

(56) References Cited

U.S. PATENT DOCUMENTS

| | | | |
|---|---|---|---|
| 2022/0362241 | A1 | 11/2022 | Davis et al. |
| 2023/0372336 | A1 | 11/2023 | Dutheil et al. |

FOREIGN PATENT DOCUMENTS

| | | |
|---|---|---|
| WO | WO 2000/048610 | 8/2000 |
| WO | WO 2000/064899 | 11/2000 |
| WO | WO 2017/117514 | 7/2017 |

OTHER PUBLICATIONS

Balbach et al., "Pharmaceutical evaluation of early development candidates 'the 100 mg-approach'", International Journal of Pharmaceutics, vol. 275, p. 1-12 (2004).

Barman et al., "Newer Antipsychotics: Brexpiprazole, Cariprazine, and Lumateperone: A Pledge or Another Unkept Promise?," World J. Psychiatr., vol. 11, No. 12, p. 1228-1238, (2021).

Bechtold et al., "Circadian Dysfunction in Disease," *Trends in Pharmacological Sciences*, vol. 31, No. 5, pp. 191-198, (2010); DOI: 10.1016/j.tips.2010.01.002.

Bennett et al., "Cecil Textbook of Medicine," 20th Edition, vol. 1, pp. 1004-1010, (1996).

Bremner et al., "Neuroimaging of Posttraumatic Stress Disorder", Psychiatric Annals Journal, vol. 28, Issue 8, p. 445-450, (1998).

Byrn et al., "Pharmaceutical Solids: A Strategic Approach to Regulatory Considerations", Pharmaceutical Research, vol. 12, No. 7, p. 945-954 (1995).

Calabrese et al., "Efficacy and Safety of Lumateperone for Major Depressive Episodes Associated with Bipolar I or Bipolar II Disorder: A Phase 3 Randomized Placebo-Controlled Trial," Am J Psychiatry, vol. 178, No. 12, p. 1098-1106, (2021).

Correll et al., "Efficacy and Safety of Lumateperone for Treatment of Schizophrenia: A Randomized Clinical Trial," JAMA Psychiatry, vol. 77, No. 4, p. 349-358 (2020).

Darmani et al., "Do Functional Relationships Exist Between 5-HT$_{1A}$ and 5-HT$_2$ Receptors?," *Pharmacology and Biochemistry & Behavior*, vol. 36, p. 901-906, (1990).

Davis et al., "ITI-007 in the treatment of schizophrenia: from novel pharmacology to clinical outcomes," Expert Review of Neurotherapeutics, vol. 16, No. 6, pp. 601-614 (2016).

Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).

Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).

Davis, et al., "ITI-007 demonstrates brain occupancy at serotonin 5-HT2A and dopamine D2 receptors and serotonin transporters using positron emission tomography in healthy volunteers," *Psychopharmacology*, vol. 232, pp. 2863-2872, (2015); DOI: 10.1007/s00213-015-3922-1.

Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93.

Edinoff et al., "Lumateperone for the Treatment of Schizophrenia," Psychopharmacology Bulletin, vol. 50, No. 4, p. 32-59 (2020).

Gramigna, J, "Lumateperone Safe, Effective for Depressive Symptoms Among Patients with Bipolar Disorders," *American Society of Clinical Psychopharmacology Annual Meeting*, Jun. 2, 2020, 3 pages.

Guillory, J.K., "Generation of Polymorphs, Hydrates, Solvates, and Amorphous Solids", Polymorphism in Pharmaceutical Solids, Chapter 5, p. 183-226 (1999).

Hackam, D., et al., "Translation of Research Evidence from Animals to Humans", JAMA, vol. 296, No. 14, p. 1731-1732 (2006).

Harbert, C.A. et al., "Neuroleptic Activity in 5-Aryltetrahydro-γ-carbolines", *J. Med. Chem.*, vol. 23, pp. 635-643 (1980).

Harvey, et al., "Lumateperone Improves Negative Symptoms Related to Emotional Experience (Avolition) in Patient with Schizophrenia," Abstract presented at the American Society of Clinical Psychopharmacology (ASCP) Annual Meeting; May 29-Jun. 1, 2018; Miami, FL.

Hlavinka, E., "Schizophrenia Tx Eases Depression in Bipolar Disorder: Lumateperone Offers Greater Rate of Response, Remission versus Placebo," *Medpage Today*, 7 pages, (2020); https://www.medpagetoday.com/meetingcoverage/psychcongress/88584.

International Search Report issued in International Application No. PCT/US2020/041063, mailed Oct. 8, 2020, 3 pages.

Kendrick, "The Newer, 'Atypical' Antipsychotic Drugs—Their Development and Current Therapeutic Use," British J. General Practice, vol. 49, p. 745-749 (1999).

Kessler, R.C., et al., "Lifetime Prevalence and Age-of-Onset Distributions of DSM-IV Disorders in the National Comorbidity Survey Replication", Arch Gen Psychiatry; vol. 62, p. 593-602, (2005).

Khorana, N., et al., "Gamma-Carbolines: Binding at 5-HT5A Serotonin Receptors", *Bioorganic & Medicinal Chemistry*, vol. 11, pp. 717-722, p. 718 Table 1, (2003).

Kumar et al., "Lumateperone: A New Treatment Approach for Neuropsychiatric Disorders," Drugs of Today, vol. 54, No. 12, p. 713-719, (2018).

Lammers, et al., "Risperidone Long-acting Injection in Schizophrenia Spectrum Illnesses Compared to First Generation Depot Antipsychotics in an Outpatient Setting in Canada," BMC Psychiatry, vol. 13, No. 155, 9 pages, (2013); http://www.biomedcentral.com/1471-244X/13/155.

Lee, T., et al. "Novel, Highly Potent, Selective 5-HT$_{2A}$/D$_2$ Receptor Antagonists as Potential Atypical Antipsychotics," *Bioorg. Med. Chem. Lett*. vol. 13, pp. 767-770, (2003).

Li et al., "Discovery of a Tetracyclic Quinoxaline Derivative as a Potent and Orally Active Multifunctional Drug Candidate for the Treatment of Neuropsychiatric and Neurological Disorders", Journal of Medicinal Chemistry, vol. 57, p. 2670-2682 (2014).

Lieberman, J.A., et al., "ITI-007 for the Treatment of Schizophrenia: A 4-Week Randomized, Double-Blind, Controlled Trial," *Biol. Psychiatry*, vol. 79, No. 12, pp. 952-961, (2015).

Lipschitz, D.S., et al., "Childhood Posttraumatic Stress Disorder: A Review of Neurobiologic Sequelae", Psychiatric Annals Journal, vol. 28, Issue 8, p. 452-457, (1998).

Makadia et al., "Poly Lactic-co-Glycolic Acid (PLGA) as Biodegradable Controlled Drug Delivery Carrier," *Polymers (Basel)*, vol. 3, No. 3, pp. 1377-1397, (2011).

Marek et al. Synergistic Action of 5-HT2A Antagonists and Selective Serotonin Reuptake Inhibitors in Neuropsychiatric Disorders. Neuropsychopharmacology, 2003. vol. 28, pp. 402-412. (Year: 2003).

McIntyre et al., "Rapid-acting Antidepressants in Psychiatry: Psychedelics, Episodic Treatments, Innovation, and Clarion Call for Methodologic Rigor in Drug Development," Expert Opinion on Drug Safety, vol. 21, No. 6, p. 715-716, (2022).

Medisorb Fact Sheet in Medisorb Microspheres Technology (Jan. 2009) at https://static.secure.website/wscfus/6472891/uploads/Medisorb.pdf (retrieved from the internet May 18, 2020) (Year: 2009).

Mueller, et al., "Detection of Depression in Acute Schizophrenia: Sensitivity and Specificity of 2 Standard Observer Rating Scales," *Can J Psychiatry*, vol. 51, No. 6, pp. 387-392, (2006).

National Library of Medicine U.S., "History of Changes for Study: NCT03249376, Lumateperone Monotherapy for the Treatment of Bipolar Depression Conducted Globally," National Institute of Health, (2019), https://clinicaltrials.gov/ct2/history/NCT03249376?V_5=View#StudyPageTop (retrieved from the internet Apr. 14, 2021); 4 pages.

(56) References Cited

OTHER PUBLICATIONS

O'Gorman, et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).
Perlis et al., "Clinical Features of Bipolar Depression Versus Major Depressive Disorder in Large Multicenter Trials", Am J Psychiatry, vol. 163, p. 225-231, (2006).
Pine, A., et al., "Dopamine, Time, and Impulsivity in Humans," *The Journal of Neuroscience*, vol. 30, No. 26, pp. 8888-8896.
Press Release, "Intra-Cellular Therapies Announces Additional Results from Phase I/II Clinical Trail for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
Press Release, "Intra-Cellular Therapies Presents Data on Symptom Improvement by Lumateperone on Negative Symptoms, Depression, and Social Function in Patients with Schizophrenia at the American Society of Clinical Psychopharmacology (ASCP) Annual Meeting," Intra-Cellular Therapies, Press Release Date: May 31, 2018, (https://ir.intracellulartherapies.com/newsreleases/.
Press Release, "Intra-Cellular Therapies Announces Positive Top-Line Results from a Phase 3 Trial of Lumateperone in Patient with Bipolar Depression," Intra-Cellular Therapies, Press Release Date: Jul. 8, 2019.
PubChem, Open Chemistry Database, PubChem SID 103920954, PubChem CID 90655118, (2011), 6 pages.
Rackova, L., et al., "Free Radical Scavenging and Antioxidant Activities of Substituted Hexahydropyridoindoles. Quantitative Structure-Activity Relationships." *Journal of Medicinal Chemistry*, vol. 49, No. 8, p. 2543-2548, (2006).
Rainer, M.K., "Risperidone long-acting injection: a review of its long term safety and efficacy," *Neuropsychiatric Disease and Treatment*, vol. 4, No. 5, pp. 919-927 (2008).
Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).
Satlin, et al., "ITI-007 (Lumateperone) for the Treatment of Agitation in Patients with Dementia, including Alzheimer's Disease," Poster P2-032, Alzheimer's Assoc. International Conference 2018 (2018).
Savjani, K., et al., "Drug Solubility: Importance and Enhancement Techniques", International Scholarly Research Network Pharmaceutics, vol. 2012, pp. 1-10, (2012).
Seishinkei Shi, vol. 110, No. 7, pp. 557-584, (2008). Partial English translation only.
Sigel, H., et al., "Tenary Complexes in Solution", *Inorganic Chemistry*, vol. 13, No. 2, p. 462-465 (1974).
Singhal, D., et al., "Drug polymorphism and dosage form design: a practical perspective," *Advanced Drug Delivery Reviews*, vol. 56, pp. 335-347 (2004).
Snyder, G.L., et al., "Functional profile of a novel modulator of serotonin, dopamine, and glutamate neurotransmission," *Psychopharmacology*, vol. 232, p. 605-621 (2015) Published online Aug. 2014, DOI 10.1007/s00213-014-3704-1.
Taragano, F.E., et al., "A Double-Blind, Randomized, Fixed-Dose Trial of Fluoxetine vs. Amitriptyline in the Treatment of Major Depression Complicating Alzheimer's Disease," Psychosomatics, vol. 38, Issue 3, p. 246-252, (1997).
Tohen, M., et al., "Efficacy of Olanzapine and Olanzapine-Fluoxetine Combination in the Treatment of Bipolar I Depression," Arch Gen Psychiatry, vol. 60, pp. 1079-1088, (2003).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Vanover, et al., "Dopamine D2 receptor occupancy of lumateperone (ITI-007): a Positron Emission Tomography Study in patients with schizophrenia," Neuropsychopharmacology 44:598-605, (2019).
Vanover, K., et al., "ITI-007: A Novel Therapy for the Treatment of Schizophrenia and Related Psychoses," *International Clinical Psychopharamcology*, vol. 26, e56, 1 page, (2011).
Vloeberghs, E., et al., "Altered Circadian Locomotor Activity in APP23 Mice: A Model for BPSD Disturbances," *European Journal of Neuroscience*, vol. 20, pp. 2757-2766, (2004); DOI: 10.1111/j.1460-9568.2004.03755.x.
Vyas, P., et al., "An Evaluation of Lumateperone Tosylate for the Treatment of Schizophrenia," *Expert Opinion on Pharmacotherapy*, vol. 21, No. 2, pp. 139-145, (2020); https://doi.org/10.1080/14656566.2019.1695778.
Wang et al., "Rapid-acting Antidepressants Targeting Modulation of the Glutamatergic System: Clinical and Preclinical Evidence and Mechanisms," General Psychiatry, vol. 35, No. e100922, 6 pages, (2022).
Warner-Schmidt, et al., "Antidepressant Effects of Selective Serotonin Reuptake Inhibitors (SSRIs) are Attenuated by Antiinflammatory Drugs in Mice and Humans," *PNAS*, vol. 108, No. 22, pp. 9262-9267, (2011).
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Weschules, D., et al., "Acetylcholinesterase Inhibitor and N-Methyl-D-Aspartic Acid Receptor Antagonist Use among Hospice Enrollees with a Primary Diagnosis of Dementia", *Journal of Palliative Medicine*, vol. 11, No. 5, pp. 738-745 (2008).
Yatham, LN, "A clinical review of aripiprazole in bipolar depression and maintenance therapy of bipolar disorder," J. Affect. Disord., vol. 128, Suppl 1: s21-8, (2011).
Zhang, G., et al., "The Role of Serotonin 5-HT2A Receptors in Memory and Cognition," *Front. Pharmacol.*, vol. 6, No. 225, pp. 1-17, (2015); DOI: 10.3389/fphar.2015.00225.
Anonymous, "Managing Depressive Symptoms in Substance Abuse Clients During Early Recovery: A Treatment Improvement Protocol TIP 48," Substance Abuse and Mental Health Services Administration, 163 pages, (2008).
Anonymous, "Bipolar Disorder," The Mayo Clinic, obtained from https://www.mayoclinic.org/diseases-conditions/bipolar-disorder/symptoms-causes/syc-20355955 on Jan. 9, 2024, 9 pages.
Anonymous, "Bipolar Disorder," The Cleveland Clinic, obtained from https://my.clevelandclinic.org/health/diseases/9294-bipolar-disorder on Jan. 9, 2024, 26 pages.
Koprowski, "What is the difference between major depressive disorder and depression?" MedicalNewsToday, https://www.medicalnewstoday.com/articles/major-depressive-disorder-vs-depression, Oct. 6, 2023 (last accessed Mar. 7, 2024).
Mahmood et al., "Serotonin and Bipolar Disorder," Journal of Affective Disorders, vol. 66, p. 1-11, (2001).
Mayo Clinic Press Editors, "Depression's new directions," Mayo Clinic Press, Feb. 6, 2024, retrieved from https://mcpress.mayoclinic.org/major-depressive-disorder/depressions-new-directions/ (last accessed Mar. 7, 2024).
McIntyre et al., "The Efficacy of Lumateperone in Patients with Bipolar Depression with Mixed Features," J Clin Psychiatry, vol. 84, No. 3, 10 pages, (2023).
McIntyre et al., "The Efficacy of Lumateperone on Symptoms of Depression in Bipolar I and Bipolar II Disorder: Secondary and Post Hoc Analyses," European Neuropsychopharmacology, vol. 68, p. 78-88, (2023).
Nelson, J.C., "A Review of the Efficacy of Serotonergic and Noradrenergic Reuptake Inhibitors for Treatment of Major Depression," Biol Psychiatry, vol. 46, p. 1301-1308, (1999).
Newton, W., "Intra Intra-Cellular reports positive Phase III trial of Caplyta in MDD and bipolar depression," ClinicalTrials Arena,

(56) References Cited

OTHER PUBLICATIONS

Mar. 29, 2023, retrieved from https://www.clinicaltrialsarena.com/news/news-intra-cellular-positive-phase-iii-trial/ (last accessed, Mar. 7, 2024).

Papakostas et al., "Inadequate Response to Antidepressant Treatment in Major Depressive Disorder," Psychiatry.com, also J. Clin. Psychiatry 81(3) (2020), retrieved from https://www.psychiatrist.com/jcp/inadequate-response-antidepressant-treatment-major (last accessed, Mar. 7, 2024).

Rapaport et al., "Relapse Prevention and Bipolar Disorder: A Focus on Bipolar Depression," Focus, vol. 1, No. 1, p. 15-31, (2003).

Su et al., "Effects of Formulation Parameters on Encapsulation Efficiency and Release Behavior of Risperidone Poly(D,L-lactide-co-glycolide) Microsphere," Chem Pharm Bull., vol. 57, No. 11, p. 1251-1256, (2009).

Zaragoza Dörwald et al., "Side Reactions in Organic Synthesis: A Guide to Successful Synthesis Design," Wiley-VCH, 6 pages, (2005).

"Clinical Trial Evaluating ITI-007 (Lumateperone) as a Monotherapy for the Treatment of Bipolar Depression," ClinicalTrials.gov, 8 pages, Nov. 9, 2015.

"Clinical Trial Evaluating ITI-007 (Lumateperone) as a Monotherapy for the Treatment of Bipolar Depression," ClinicalTrials.gov, 5 pages, Nov. 9, 2015.

\* cited by examiner

METHODS

CROSS-REFERENCE TO RELATED APPLICATIONS

This application is a continuation of application Ser. No. 16/922,893, filed on Jul. 7, 2020, which claims priority to and the benefit of U.S. provisional application No. 62/871,170, filed on Jul. 7, 2019, the contents of each of which are hereby incorporated by reference in their entireties.

TECHNICAL FIELD

The present disclosure relates to use of lumateperone, in free or pharmaceutically acceptable salt form, optionally in deuterated form, for the treatment of Bipolar II Disorder.

BACKGROUND

Substituted heterocycle fused gamma-carbolines such as lumateperone are known to be $5\text{-HT}_{2A}$ or $5\text{-HT}_{2A}$/D2 receptor ligands, which are useful in treating central nervous system disorders. These compounds antagonize the serotonin-2A ($5\text{-HT}_{2A}$) receptor, and/or modulate dopamine receptor signaling at the level of key intra-cellular phosphoproteins. Such compounds are principally known to be useful for the treatment of positive and negative symptoms of schizophrenia. At dopamine D2 receptors, these compounds have dual properties and act as both post-synaptic antagonists and pre-synaptic partial agonists. They also stimulate phosphorylation of glutamatergic NMDA NR2B, or GluN2B, receptors in a mesolimbic specific manner. It is believed that this regional selectivity in the brain areas thought to mediate the efficacy of antipsychotic drugs, together with the serotonergic, glutamatergic, and dopaminergic interactions, may result in antipsychotic efficacy for positive, negative, affective and cognitive symptoms associated with schizophrenia. The compounds also exhibit serotonin reuptake inhibition, providing antidepressant activity for the treatment of schizoaffective disorder, co-morbid depression, and/or as a stand-alone treatment for major depressive disorder. The $5\text{-HT}_{2A}$ or $5\text{-HT}_{2A}$/D2 receptor ligands as described are also useful for the treatment of bipolar disorder and other psychiatric and neurodegenerative disorders, particularly behavioral disturbances associated with dementia, autism and other CNS diseases. These features may be able to improve the quality of life of patients with schizophrenia and enhance social function to allow them to more fully integrate into their families and their workplace. These compounds display differential dose-dependent effects, selectively targeting the $5\text{-HT}_{2A}$ receptor at low doses, while progressively interacting with the D2 receptor at higher doses. As a result, at lower doses, they are useful in treating sleep, aggression and agitation. At a high-dose, they can treat acute exacerbated and residual schizophrenia, bipolar disorders, and mood disorders.

Lumateperone, which is 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone, having the formula:

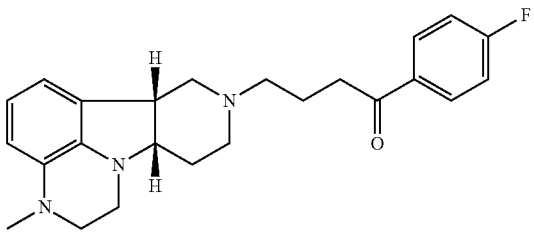 [SMILES: CN1CCN2c3c(cccc31)[C@@H]1CN(CCCC(=O)c3ccc(F)cc3)CC[C@@H]12]

is a therapeutic agent now in clinical trials. Lumateperone provides selective and simultaneous modulation of serotonin, dopamine and glutamate neurotransmission. It exhibits potent (Ki=0.5 nM) $5\text{-HT}_{2A}$ receptor antagonism, activity as a mesolimbic/mesocortical-selective dopamine receptor protein phosphorylation modulator consistent with presynaptic D2 receptor partial agonism and postsynaptic D2 receptor antagonism (Ki=32 nM) in vivo, high D1 receptor affinity (Ki=52 nM), and inhibition of the serotonin transporter (SERT) (Ki=26-62 nM, using different assays for SERT activity). Lumateperone was approved by the U.S. Food & Drug Administration for the treatment of schizophrenia in 2019, and it is or has been in Phase III clinical development as a treatment for bipolar depression and agitation in dementia, including Alzheimer's Disease.

Lumateperone and related compounds have been disclosed in U.S. Pat. Nos. 6,548,493; 7,238,690; 6,552,017; 6,713,471; U.S. RE39,680, and U.S. RE39,679, as novel compounds useful for the treatment of disorders associated with $5\text{-HT}_{2A}$ receptor modulation such as anxiety, depression, psychosis, schizophrenia, sleep disorders, sexual disorders, migraine, conditions associated with cephalic pain, and social phobias. PCT/US08/03340 and U.S. Pat. No. 7,081,455 also disclose methods of making substituted heterocycle fused gamma-carbolines and uses of these gamma-carbolines as serotonin agonists and antagonists useful for the control and prevention of central nervous system disorders such as addictive behavior and sleep disorders. WO 2009/145900 and U.S. Pat. No. 8,598,119, and WO 2013/155506 and US 2015/0080404, each incorporated herein by reference, disclose the use of specific substituted heterocycle fused gamma-carbolines for the treatment of a combination of psychosis and depressive disorders as well as sleep, depressive and/or mood disorders in patients with psychosis or Parkinson's disease and for the treatment or prophylaxis of disorders associated with dementia, particularly behavioral or mood disturbances such as agitation, irritation, aggressive/assaultive behavior, anger, physical or emotional outbursts and psychosis and sleep disorders associated with dementia. WO 2009/114181 and U.S. Pat. No. 8,648,077, and US2020/0157100, each incorporated herein by reference, disclose methods of preparing toluenesulfonic acid addition salt crystals of particular substituted heterocycle fused gamma-carbolines, e.g., toluenesulfonic acid addition salt of lumateperone (mono-tosylate and bis-tosylate salts).

WO 2011/133224 and U.S. Pat. No. 8,993,572, each incorporated herein by reference, disclose prodrugs/metabolites of substituted heterocycle fused gamma-carbolines for improved formulation, e.g., extended/controlled release formulation. This application discloses that heterocycle fused gamma-carboline N-substituted with a 4-fluorophenyl(4- hydroxy)butyl moiety are shown to have high selectivity for the serotonin transporter (SERT) relative to the heterocycle fused gamma-carboline containing 4-fluorophenylbutanone.

WO 2009/145900 (and U.S. Pat. No. 8,598,119) teaches that selected substituted heterocycle fused gamma-carboline compounds have nanomolar affinity for the serotonin reuptake transporter (SERT) and so are selective serotonin reuptake inhibitors.

As disclosed in WO2015/154025, US 2017/0183350, WO 2017/165843, and US 2019/231780, each incorporated herein by reference, deuterated forms of lumateperone and related compounds have been shown to have improved metabolic stability.

According to the National Institute of Mental Health, bipolar disorder, also known as manic-depressive illness, is a brain disorder that causes unusual shifts in mood, energy, activity levels, and the ability to carry out day-to-day tasks. There are four basic types of bipolar disorder; all of them involve clear changes in mood, energy, and activity levels. These moods range from periods of extremely "up," elated, and energized behavior (known as manic episodes) to very sad, "down," or hopeless periods (known as depressive episodes). Less severe manic periods are known as hypomanic episodes.

a. Bipolar I Disorder—defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible.

b. Bipolar II Disorder—defined by a pattern of depressive episodes and hypomanic episodes, but not the full-blown manic episodes described above.

c. Cyclothymic Disorder (also called cyclothymia)—defined by numerous periods of hypomanic symptoms as well numerous periods of depressive symptoms lasting for at least 2 years (1 year in children and adolescents). However, the symptoms do not meet the diagnostic requirements for a hypomanic episode and a depressive episode.

d. Other Specified and Unspecified Bipolar and Related Disorders—defined by bipolar disorder symptoms that do not match the three categories listed above.

The etiology of bipolar disorder remains unclear, and the disorder remains resistant to treatment. Pharmaceutical treatments include mood stabilizing drugs, such as lithium or anticonvulsants (e.g., carbamazepine, lamotrigine, and valproate). Conventional antidepressants, such as selective serotonin reuptake inhibitors (SSRIs) are not only less effective for treating bipolar depression than for major depressive disorder, but they may do harm, by triggering manic episodes and rapid cycling.

Antipsychotic medications are generally effective for short-term treatment of bipolar manic episodes in Bipolar I Disorder, but they are generally ineffective in treating Bipolar II Disorder and in maintenance treatment during depressive episodes. Moreover, many antipsychotic medications exhibit significant side effects, such as extrapyramidal symptoms including acute dyskinesias and dystonic reactions, tardive dyskinesia, Parkinsonism, akinesia, akathisia, and neuroleptic malignant syndrome.

For example, the atypical antipsychotic aripiprazole was extensively evaluated for treatment of bipolar disorder, but a review of the clinical data concluded: "Although aripiprazole has proven efficacy for acute mania and the prevention of mania, the evidence available thus far does not support the efficacy of aripiprazole for the treatment of acute bipolar depression and prevention of depressive relapse." Yatham L N, "A clinical review of aripiprazole in bipolar depression and maintenance therapy of bipolar disorder." *J. Affect. Disord.* 2011 January; 128 Suppl 1:S21-8. Aripiprazole is currently approved in the United States for "Acute Treatment of Manic and Mixed Episodes associated with Bipolar I." It is not currently approved to treat Bipolar II Disorder.

While there are many antipsychotic agents approved to treat mania associated with Bipolar I Disorder, only four antipsychotic agents are currently approved in the United States to treat depression associated with Bipolar I Disorder, and only one antipsychotic agent is currently approved in the United States to treat Bipolar II Disorder, quetiapine (Seroquel®). Quetiapine, however, has been reported to be highly sedating and to cause a number of metabolic side effects such as hyperglycemia, dyslipidemia, and weight gain. It also has been associated with emergence of suicidal thoughts in some patients.

Estimates vary, but it is believed that approximately 30-60% of patients suffering from bipolar disorders suffer from Bipolar II Disorder. Despite its prevalence, Bipolar II Disorder is often misdiagnosed as either Major Depressive Disorder or Bipolar I Disorder, and improperly treated as a result. There is a need for safer and more effective treatments for Bipolar II Disorder, as well as a need for therapies effective to treat both Bipolar I Disorder and Bipolar II Disorder.

BRIEF SUMMARY

We have surprisingly found that lumateperone is useful to treat Bipolar II Disorder. Clinical results suggest that lumateperone is at least as effective in this indication as existing antipsychotic agents in treating bipolar disorders, with particularly unexpected efficacy in Bipolar II Disorder, which is often resistant to treatment with antipsychotic agents. Moreover, lumateperone exhibits a favorable safety profile. The clinical trials demonstrate that, unlike many other antipsychotic agents, lumateperone does not increase akathisia, restlessness, or other movement disorders, it does not increase suicidal ideation, and it does not have significant metabolic side effects.

Accordingly, in a first aspect, the present disclosure provides a method for treating Bipolar II Disorder in a patient in need thereof, comprising administering a therapeutically effective amount of lumateperone, in free base or pharmaceutically acceptable salt form, optionally in deuterated form, to a patient in need thereof.

Further embodiments will be apparent from the following detailed description and examples.

DETAILED DESCRIPTION

In a Phase 3 clinical trial evaluating lumateperone as monotherapy in the treatment of major depressive episodes associated with Bipolar I or Bipolar II disorder, lumateperone 42 mg daily (administered orally as 60 mg of the tosylate salt) met the primary endpoint for improvement in depression as measured by change from baseline versus placebo on the Montgomery-Åsberg Depression Rating Scale (MADRS) total score (p<0.001; effect size=0.56), as well as its key secondary endpoint, Clinical Global Impression Scale for Bipolar for Severity of Illness (CGI-BP-S) Total Score (p<0.001; effect size=0.46).

Moreover, the patients did not exhibit emergence of mania as measured by the Young Mania Rating Scale (YMRS) and a specific clinical global impression of severity for mania, meaning that the drug was effective in preventing the emergence of mania or hypomania, and did not trigger manic episodes or cause rapid cycling that is often linked to SSRIs in treatment of bipolar disorders.

Unexpectedly, in view of the generally limited efficacy of antipsychotics in Bipolar II Disorder, a subgroup analysis of patients with Bipolar II disorder showed that lumateperone at 42 mg daily was statistically significant superior versus placebo on the MADRS total score.

Lumateperone demonstrated a favorable safety profile in this trial, comparable to placebo. Unlike quetiapine, lumateperone did not appear to have any noticeable metabolic effects, such as such as hyperglycemia, dyslipidemia, or weight gain. There were no adverse event reports of suicidal ideation, no suicides, and no discontinuations due to suicidal thoughts. Equally important, there were also no adverse event reports of extrapyramidal symptoms, such as akathisia, restlessness, or other motor side effects.

Akathisia has been associated with the use of most antipsychotic and antidepressant drugs, particularly in bipolar disorders. Akathisia has been linked to suicide. This highlights the clinical importance of lumateperone, as it can treat Bipolar II Disorder without causing akathisia and is therefore less likely to cause suicidal behaviors.

In a first aspect, the present disclosure provides a method (Method 1) for the treatment of Bipolar II Disorder, comprising administering to a patient in need thereof, a therapeutically effective amount of lumateperone, in free base or pharmaceutically acceptable salt form, optionally in deuterated form. In further embodiments of the first aspect, the present disclosure provides:

1.1. Method 1, wherein the lumateperone is in the form of the tosylate salt (e.g., an acid addition salt of toluenesulfonic acid, such as a mono-tosylate salt or bis-tosylate salt), optionally wherein the salt is a solid crystalline salt, such as those disclosed in US 2011/112105 and/or US 2020/0157100, the contents of each of which are incorporated by reference herein in their entireties.

1.2. Method 1, wherein lumateperone is in the form of the free base.

1.3. Any foregoing method wherein the lumateperone is in deuterated form, e.g., wherein the deuterium: protium ratio for a specified carbon-bound hydrogen atom is significantly higher, e.g., at least 2×, for example at least 10× higher, than the natural isotope ratios.

1.4. Method 1.3 wherein the lumateperone is in deuterated form selected from:

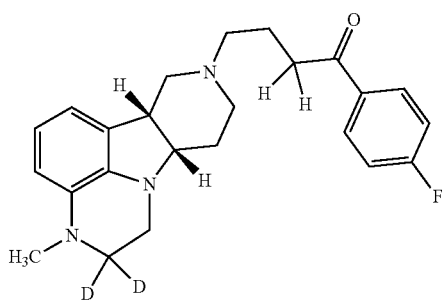

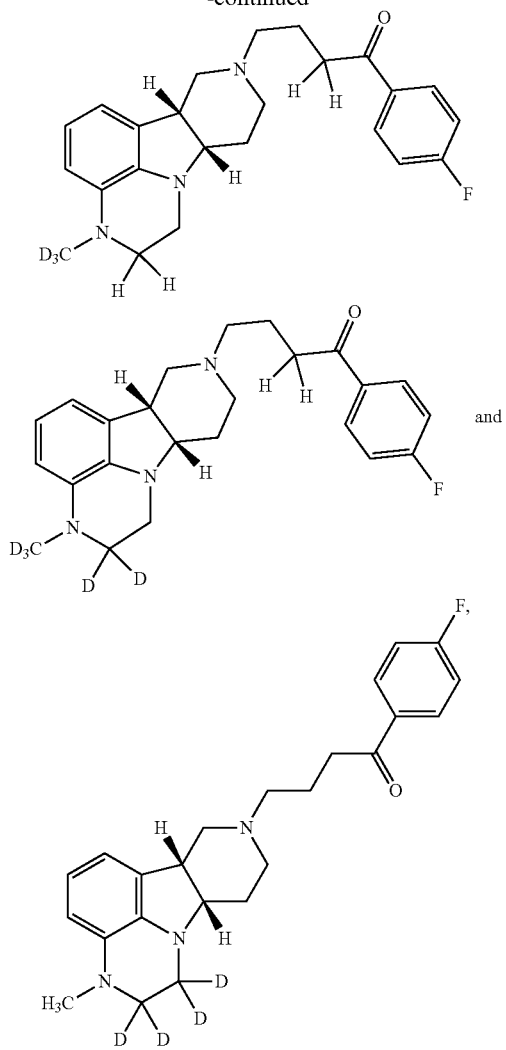

wherein D represents a hydrogen position with substantially greater than natural deuterium incorporation (i.e., substantially greater than 0.0156%), e.g., greater than 60%, or greater than 70%, or greater than 80%, or greater than 90% or greater than 95%, or greater than 96%, or greater than 97%, or greater than 98%, or greater than 99%, in free or pharmaceutically acceptable salt form, e.g. tosylate salt form.

1.5. Any foregoing method, wherein the lumateperone, in free or pharmaceutically acceptable salt form, optionally in deuterated form, is administered in a total daily dose equivalent to 6 to 60 mg of free base, e.g., equivalent to 20-50 mg of free base.

1.6. Any foregoing method, wherein the lumateperone, in free or pharmaceutically acceptable salt form, optionally in deuterated form, is administered in a total daily dose equivalent to 25-30 mg of free base.

1.7. Any foregoing method, wherein the lumateperone, in free or pharmaceutically acceptable salt form, optionally in deuterated form, is administered in a total daily dose equivalent to 40-45 mg of free base.

1.8. Any foregoing method, wherein the method comprises once daily administration of a unit dosage for oral administration, for example a tablet or capsule, comprising about 42 mg of lumateperone free base equivalent, in free or pharmaceutically acceptable salt form, optionally in deuterated form, in combination or association with a pharmaceutically acceptable diluent or carrier.

1.9. Any foregoing method, wherein the method comprises once daily administration of a tablet or capsule comprising about 60 mg of lumateperone tosylate optionally in deuterated form, in combination or association with a pharmaceutically acceptable diluent or carrier.

1.10. Any foregoing method, wherein the method comprises once daily administration of a unit dosage for oral administration, for example a tablet or capsule, comprising about 28 mg of lumateperone free base equivalent, in free or pharmaceutically acceptable salt form, optionally in deuterated form, in combination or association with a pharmaceutically acceptable diluent or carrier.

1.11. Any foregoing method, wherein the method comprises once daily administration of a tablet or capsule comprising about 40 mg of lumateperone tosylate optionally in deuterated form, in combination or association with a pharmaceutically acceptable diluent or carrier.

1.12. Any foregoing method, wherein the method comprises once daily administration of a unit dosage for subcutaneous or transmucosal administration, e.g., a sublingual or buccal orally disintegrating tablet or film, comprising lumateperone in free or pharmaceutically acceptable salt form, optionally in deuterated form, in an amount equivalent to 10-60 mg of free base, and a pharmaceutically acceptable diluent or carrier.

1.13. Any foregoing method wherein the method comprises administration of lumateperone, in free or pharmaceutically acceptable salt form, optionally in deuterated form, in a long acting injectable form.

1.14. Any foregoing method wherein the patient has been diagnosed with Bipolar II Disorder.

1.15. Any foregoing method wherein the condition to be treated is depression in Bipolar II Disorder, or a depressive episode associated with Bipolar II Disorder (e.g., a major depressive episode).

1.16. Any foregoing method wherein the condition to be treated includes mixed affective episodes in Bipolar II Disorder.

1.17. Any foregoing method wherein the condition to be treated includes hypomanic episodes.

1.18. Any foregoing method wherein the treatment suppresses mania or hypomania.

1.19. Any foregoing method wherein the treatment does not trigger manic or hypomanic episodes or rapid cycling.

1.20. Any foregoing method wherein, during the course of treatment, the patient does not exhibit emergence of mania or hypomania as measured by the Young Mania Rating Scale (YMRS).

1.21. Any foregoing method wherein, during the course of treatment, the patient shows improvement in depressive symptoms, e.g., as measured using one or more of the Montgomery-Åsberg Depression Rating Scale (MADRS), the Hamilton Depression Rating Scale (HAM-D), the Beck Depression Inventory (BDI), the Zung Self-Rating Depression Scale, the Wechsler Depression Rating Scale, the Raskin Depression Rating Scale, the Inventory of Depressive Symptomatology (IDS), or the Quick Inventory of Depressive Symptomatology (QIDS)

1.22. Any foregoing method wherein, during the course of treatment, the patient shows improvement in the Montgomery—Åsberg Depression Rating Scale (MADRS) total score (e.g., improvement within 8 days or less after initiation of treatment).

1.23. Any foregoing method wherein, following treatment, the patient shows improvement in Clinical Global Impression Scale for Bipolar for Severity of Illness (CGI-BP-S) (e.g., improvement within 8 days or less after initiation of treatment).

1.24. Any foregoing method wherein, during the course of treatment, the patient shows improvement in Clinical Global Impression Scale for Bipolar Depression for Severity of Illness (CGI-BP-Depression-S) (e.g., improvement within 8 days or less after initiation of treatment).

1.25. Any foregoing method wherein, during the course of treatment, the patient does not show an increase in Clinical Global Impression Scale for Bipolar Mania for Severity of Illness (CGI-BP-Mania-S).

1.26. Any foregoing method wherein, during the course of treatment, the patient shows improvement in overall mental health, e.g., as measured using Clinical Global Impression—Severity (CGI-S) or Clinical Global Impression-Improvement (CGI-I) (e.g., improvement within 8 days or less after initiation of treatment).

1.27. Any foregoing method wherein the treatment does not result in metabolic side effects, e.g., does not result in one or more of hyperglycemia, dyslipidemia, or weight gain.

1.28. Any foregoing method wherein the treatment does not induce suicidal ideation or suicidal thoughts.

1.29. Any foregoing method wherein the treatment does not induce extrapyramidal symptoms, e.g., one or more of akathisia, akinesia, restlessness, acute dyskinesia, dystonic reactions, tardive dyskinesia, Parkinson's-like symptoms, or neuroleptic malignant syndrome.

1.30. Any foregoing method wherein the treatment does not induce akathisia.

1.31. Any foregoing method wherein the lumateperone in free base or pharmaceutically acceptable salt form, optionally in deuterated form, is administered as monotherapy for treatment of Bipolar II Disorder.

1.32. Any foregoing method wherein the patient is concurrently receiving a mood-stabilizing agent, e.g., selected from lithium, carbamazepine, oxcarbazepine, lamotrigine, and valproate (including divalproex (a.k.a. valproate semisodium), sodium valproate, and other free, salt or complexed forms of valproic acid).

1.33. Any foregoing method wherein the patient is concurrently receiving lithium or valproate.

1.34. Any foregoing method wherein the patient is under the age of 18.

1.35. Any foregoing method wherein the patient is an adult, e.g., over the age of 18, e.g., between the ages of 18 and 75, inclusive.

1.36. Any foregoing method wherein the patient is elderly, e.g., 65 or older, e.g. 75 or older.

1.37. Any foregoing method wherein the lumateperone in free or salt form is indicated for use in the treatment of depression in Bipolar I Disorder and Bipolar II Disorder.

1.38. Any foregoing method wherein the duration of treatment is six weeks or less.

1.39. Any foregoing method wherein the treatment is a maintenance treatment.

1.40. Any foregoing method wherein the duration of treatment is six weeks or more.
1.41. Any foregoing method, wherein the patient was previously treated with an SSRI (e.g., such treatment was ineffective and/or discontinued, such as due to side effects).
1.42. Method 1.41, wherein said SSRI is selected from citalopram, escitalopram, fluoxetine, fluvoxamine, paroxetine, and sertraline.
1.43. Any foregoing method, wherein the patient was previously treated with an antipsychotic, such as an atypical antipsychotic (e.g., such treatment was ineffective and/or discontinued, such as due to side effects).
1.44. Method 1.43, wherein said antipsychotic is selected from haloperidol, aripiprazole, quetiapine, olanzapine, risperidone, lurasidone, paliperidone, iloperidone, ziprasidone, brexipiprazole, asenapine, clozapine, and zotepine.

In another aspect, the disclosure provides lumateperone, in free or pharmaceutically acceptable salt form, optionally in deuterated form, for use in the treatment of Bipolar II Disorder, e.g., for use in any of Methods 1, et seq.

In another aspect, the disclosure provides the use of lumateperone, in free or pharmaceutically acceptable salt form, optionally in deuterated form, in the manufacture of a medicament for the treatment of Bipolar II Disorder, e.g., for use in any of Methods 1, et seq.

The words "treatment" and "treating" are to be understood accordingly as embracing prophylaxis and treatment or amelioration of symptoms of disease and/or treatment of the cause of the disease. In particular embodiments, the words "treatment" and "treating" refer to prophylaxis or amelioration of symptoms of the disease.

"Patient" as used herein means a human patient, unless otherwise indicated.

Pharmaceutically acceptable salts of lumateperone include pharmaceutically acceptable acid addition salts, for example, toluenesulfonic acid addition salts (tosylate salts). Tosylate salts of lumateperone include the monotosylate salt and the bis-tosylate salt. Unless otherwise indicated, the term "lumateperone tosylate" refers to the mono-tosylate salt. Lumateperone tosylate is sold as Caplyta™. Where dosages or amounts of a salt are given by weight, e.g., milligrams per day or milligrams per unit dose, the dosage amount of the salt is given as the weight of the corresponding free base, unless otherwise indicated.

The term "concurrently" when referring to a therapeutic use refers to administration of two or more active ingredients to a patient as part of a regimen for the treatment of a disease or disorder, whether the two or more active agents are given at the same or different times or whether given by the same or different routes of administrations. Concurrent administration of the two or more active ingredients may be at different times on the same day, or on different dates or at different frequencies.

Dosages employed in practicing the present disclosure will of course vary depending, e.g. on the particular disease or condition to be treated, the particular active compounds used, the mode of administration, and the therapy desired. Lumateperone, in free or pharmaceutically acceptable salt form, optionally in deuterated form, may be administered by any suitable route, including oral, parenteral, transdermal, or transmucosal, for example in the form of a tablet, a capsule, a subcutaneous injection, long acting injectable (depot), or an oral, rapidly disintegrating tablet or film for sublingual or buccal administration.

In some embodiments, lumateperone is provided as a tablet or capsule for oral administration, comprising lumateperone tosylate in combination with a pharmaceutically acceptable diluent or carrier.

In some embodiments, lumateperone is provided as a rapidly disintegrating tablet or film for sublingual or buccal administration, comprising lumateperone tosylate in combination with a pharmaceutically acceptable diluent or carrier.

In some embodiments, lumateperone, in free or pharmaceutically acceptable salt form, optionally in deuterated form, is administered as a depot formulation, e.g., by dispersing, dissolving, suspending, or encapsulating the compound in a polymeric matrix as described in herein, such that the compound is continually released as the polymer degrades over time. The release of the lumateperone from the polymeric matrix provides for the controlled- and/or delayed- and/or sustained-release, e.g., from the pharmaceutical depot composition, into a subject, for example a warm-blooded animal such as man, to which the pharmaceutical depot is administered. Thus, the pharmaceutical depot delivers lumateperone to the subject at concentrations effective for treatment of the particular disease or medical condition over a sustained period of time, e.g., 1 week to 3 months.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethylene glycol copolymer or polyglycolic acid-polyethylene glycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylene propylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer, such as PLGA 50:50, PLGA 85:15 and PLGA 90:10

In one such embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly(glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. One suitable polymer for use in the practice of this invention is dl(polylactide-co-glycolide). In one embodiment, the molar ratio of lactide to glycolide in such a copolymer be in the range of from about 75:25 to 50:50.

Useful PLGA polymers may have a weight-average molecular weight of from about 5,000 to 500,000 Daltons, preferably about 150,000 Daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

For the avoidance of doubt, any disclosure of a numerical range, e.g., "up to X" amount is intended to include the upper numerical limit X. Therefore, a disclosure of "up to 60 mg" is intended to include 60 mg.

All references cited herein are hereby incorporated by referenced in their entireties. In the event of a conflict in a definition in the present disclosure and that of a cited reference, the present disclosure controls.

The disclosure is further illustrated in the following examples, which are meant to be exemplary and not limiting.

EXAMPLE 1: CLINICAL TRIAL IN BIPOLAR I DISORDER AND BIPOLAR II DISORDER PATIENTS

A multi-center, multi-national, randomized, double-blind, fixed-dose, placebo-controlled clinical trial is conducted substantially in accordance with the following protocol.

Patients are recruited according to the following criteria:

Major Inclusion Criteria: Male or female subjects of any race, ages 18-75 inclusive, with a clinical diagnosis of Bipolar I or Bipolar II disorder, experiencing a current major depressive episode, and able to provide written informed consent.

Major Exclusion Criteria: Any female subject who is pregnant or breast-feeding, and any subject judged to be medically inappropriate for study participation.

A total of 381 patients recruited in accordance with the above criteria are randomized 1:1 to two study arms: (i) lumateperone 42 mg (administered orally as 60 mg of lumateperone tosylate) and (ii) placebo. In the lumateperone arm, lumateperone (lumateperone tosylate 60 mg) is administered once daily every evening for 6 weeks. In the placebo arm, placebo is administered once daily every evening for 6 weeks. The patients do not receive other medications for treatment of bipolar disorders. The study is quadruple-masked (i.e., to participant, care provider, investigator, and outcomes assessor).

The total study duration is about 10 weeks, including up to 2 weeks screening period (washout of prohibited medications), a 6-week double-blind treatment period, and 2-week safety follow-up period.

The primary outcome measure is the Montgomery-Åsberg Depression Rating Scale (MADRS) [Time Frame: Day 43]. Secondary outcome measures are the Clinical Global Impression Scale, Bipolar version (CGI-BP) [Time Frame: Day 43] and the Quality of Life Enjoyment and Satisfaction Questionnaire-Short Form (Q-LES-Q-SF) [Time Frame: Day 43].

A further objective of the study is to determine the safety and tolerability of lumateperone versus placebo as measured by:
a. Incidence of Adverse Events (AEs)
b. Young Mania Rating Scale (YMRS)
c. Columbia Suicide Severity Rating Scale (C-SSRS)
d. Abnormal Involuntary Movement Scale (AIMS)
e. Barnes Akathisia Rating Scale (BARS)
f. Simpson Angus Scale (SAS)
g. Clinical laboratory evaluations
h. Electrocardiograms (ECGs)
i. Vital sign measurements
j. Physical examination and neurological findings The patient disposition is as follows:

TABLE 1

|  | Lumateperone 42 mg | Placebo | Total |
| --- | --- | --- | --- |
| Screened |  |  | 546 |
| Randomized | 191 | 190 | 381 |
| Safety Population | 188 | 189 | 377 |
| Intention to Treat (ITT) Population | 188 | 188 | 376 |
| Completed, n (%) | 167 (87.4) | 166 (87.4) | 333 (87.4) |
| Discontinued, n (%) | 21 (11.0) | 23 (12.1) | 44 (11.5) |

The change seen from baseline to Day 43 in MADRS total score was as follows:

TABLE 2

| Treatment Group | Baseline n | Mean (SD) | n | LS Mean (SE) Change at Day 43 | 95% CI | Comparison to Placebo at Day 43 | | | |
|---|---|---|---|---|---|---|---|---|---|
| | | | | | | LSMD (SE) | 95% CI | Effect Size | P-Value |
| Lumateperone 42 mg N = 188 | 169 | 30.7 (4.74) | 169 | −16.7 (0.69) | (−18.06, −15.34) | 4.6 (0.89) | (−6.34, −2.83) | −0.56 | <001 |
| Placebo N = 188 | 166 | 30.2 (4.68) | 166 | −12.1 (0.68) | (−13.45, −10.79) | — | — | — | — |

The change seen from baseline to Day 43 in CGI-BP-S total score was as follows:

TABLE 3

| Treatment Group | Baseline n | Mean (SD) | n | LS Mean (SE) Change at Day 43 | 95% CI | Comparison to Placebo at Day 43 | | | |
|---|---|---|---|---|---|---|---|---|---|
| | | | | | | LSMD (SE) | 95% CI | Effect Size | P-Value |
| Lumateperone 42 mg N = 188 | 169 | 10.3 (1.10) | 169 | −3.5 (0.17) | (−3.81, −3.14) | −0.9 (0.22) | (−1.37, −0.51) | −0.46 | <001 |
| Placebo N = 188 | 166 | 10.2 (1.07) | 166 | −2.5 (0.17) | (−2.86, −2.21) | — | — | — | — |

Lumateperone 42 mg was thus superior to placebo as demonstrated by statistically significant improvements on MADRS Total Score and CGI-BP-S which were the primary and key secondary measures in this study. The improvements seen in this study with Lumateperone 42 mg are considered to be clinically meaningful.

The safety profile of lumateperone was similar to placebo. A summary of treatment-emergent adverse events (TEAEs) is as follows:

TABLE 4

| | Lumateperone 42 mg (N = 188) n (%) | Placebo (N = 189) n (%) |
|---|---|---|
| Number of Patients | | |
| With One or More TEAE | 103 (54.8) | 95 (50.3) |
| With Drug-related TEAE | 78 (41.5) | 59 (31.2) |
| With Treatment-Emergent SAE | 1 (0.5) | 0 |
| With Drug-related Treatment-Emergent SAE | 0 | 0 |
| With Treatment-Emergent Death | 0 | 0 |
| Subjects Discontinued Study | | |
| Due to TEAE | 11 (5.9) | 4 (2.1) |
| Due to Drug-related TEAE | 9 (4.8) | 2 (1.1) |
| Due to Treatment-Emergent SAE | 1 (0.5) | 0 |
| Due to Drug-related Treatment-Emergent SAE | 0 | 0 |
| Subjects who Died | 0 | 0 |

Lumateperone 42 mg was generally safe and well tolerated. The most commonly reported adverse events that were observed at a rate greater than 5% and higher than placebo were headache, somnolence and nausea. Importantly, the rates of akathisia and extrapyramidal symptoms were less than 1% and similar to placebo.

In this trial, once-daily lumateperone 42 mg met the primary endpoint with statistically significant greater improvement over placebo at week 6 (trial endpoint), as measured by change from baseline on the MADRS total score. In the intent-to-treat (ITT) study population, the least squares (LS) mean reduction from baseline for lumateperone 42 mg was 16.7 points, versus 12.1 points for placebo (LS mean difference=4.6 points; effect size=0.56, p<0.001). Moreover, lumateperone 42 mg showed statistically significant separation from placebo as early as week 1, which was maintained at every time point throughout the entire trial.

Lumateperone 42 mg also met the key secondary endpoint of statistically significant improvement on the CGI-BP-S Total Score (p<0.001; effect size=0.46) and on the CGI component that specifically assesses depression (CGI-S Depression Score; p<0.001; effect size=0.5).

These results were supported by statistically significant benefits on responder rates and remission rates, demonstrating the clinical meaningfulness of the primary outcome. In addition, in a subgroup analysis of patients with Bipolar II disorder lumateperone 42 mg was statistically significant superior to placebo on the MADRS total score.

We claim:

1. A method for the treatment of a major depressive episode associated with Bipolar II Disorder, comprising administering to a patient in need thereof, a therapeutically effective amount of lumateperone in mono-tosylate salt form, wherein the method comprises once daily administration of a tablet or capsule comprising about 60 mg of lumateperone mono-tosylate in combination or association with a pharmaceutically acceptable diluent or carrier.

2. The method of claim 1, wherein the salt is a solid crystalline salt.

3. The method of claim 1, wherein the patient also suffers from mixed affective episodes.

4. The method of claim 1, wherein the patient also suffers from hypomanic episodes.

5. The method of claim 1, wherein the method suppresses mania or hypomania.

6. The method of claim 1, wherein the method does not trigger manic or hypomanic episodes or rapid cycling.

7. The method of claim 1, wherein during the course of treatment the patient shows improvement in the Montgomery-Åsberg Depression Rating Scale (MADRS) total score and/or shows improvement in the Clinical Global Impression Scale for Bipolar for Severity of Illness (CGI-BP-S).

8. The method of claim 1, wherein the method does not result in one or more of hyperglycemia, dyslipidemia, weight gain, suicidal ideation, suicidal thoughts, or extrapyramidal symptoms.

9. The method of claim 1, wherein the patient is concurrently receiving a mood-stabilizing agent.

10. The method of claim 1, wherein the patient was previously treated with a selective serotonin reuptake inhibitor.

11. The method of claim 1, wherein the patient was previously treated with an atypical antipsychotic.

12. The method of claim 1, wherein the patient was previously treated with an antipsychotic selected from haloperidol, aripiprazole, quetiapine, olanzapine, risperidone, lurasidone, paliperidone, iloperidone, ziprasidone, brexpiprazole, asenapine, clozapine, and zotepine.

13. The method of claim 1, wherein during the course of treatment, the patient does not exhibit emergence of mania or hypomania as measured by the Young Mania Rating Scale (YMRS).

14. The method of claim 9, wherein the mood-stabilizing agent is selected from lithium, carbamazepine, oxcarbazepine, lamotrigine, and valproate.

15. The method of claim 9, wherein the mood-stabilizing agent is lithium or valproate.

16. The method of claim 15, wherein the valproate is valproate semisodium, sodium valproate, or another free, salt or complexed form of valproic acid.

17. The method of claim 7, wherein the patient shows the improvement in the MADRS total score and/or the improvement in CGI-BP-S within 8 days or less after initiation of treatment.

18. The method of claim 1, wherein the lumateperone mono-tosylate is administered as monotherapy.

19. The method of claim 1, wherein during the course of treatment the patient shows improvement in the Montgomery-Åsberg Depression Rating Scale (MADRS) total score.

20. The method of claim 1, wherein during the course of treatment the patient shows improvement in the Clinical Global Impression Scale for Bipolar for Severity of Illness (CGI-BP-S).

21. The method of claim 8, wherein the method does not result in one or more of hyperglycemia, dyslipidemia, weight gain, or extrapyramidal symptoms.

22. A method for the treatment of a depressive episode associated with Bipolar II Disorder, comprising administering to a patient in need thereof, a therapeutically effective amount of lumateperone in mono-tosylate salt form, wherein the method comprises once daily administration of a tablet or capsule comprising about 60 mg of lumateperone mono-tosylate in combination or association with a pharmaceutically acceptable diluent or carrier.

23. The method of claim 22, wherein during the course of treatment the patient shows improvement in the Montgomery-Åsberg Depression Rating Scale (MADRS) total score.

24. The method of claim 22, wherein during the course of treatment the patient shows improvement in the Clinical Global Impression Scale for Bipolar for Severity of Illness (CGI-BP-S).

25. The method of claim 22, wherein the treatment does not result in one or more of hyperglycemia, dyslipidemia, weight gain, or extrapyramidal symptoms.

26. The method of claim 22, wherein the lumateperone mono-tosylate is administered as monotherapy.

27. The method of claim 22, wherein the patient is concurrently receiving a mood-stabilizing agent selected from lithium and valproate.

* * * * *

UNITED STATES PATENT AND TRADEMARK OFFICE
CERTIFICATE OF CORRECTION

PATENT NO. : 12,090,155 B2  
APPLICATION NO. : 18/494754  
DATED : September 17, 2024  
INVENTOR(S) : Mates et al.

Page 1 of 1

It is certified that error appears in the above-identified patent and that said Letters Patent is hereby corrected as shown below:

In the Specification

Column 13-14, in Table 2, under LSMD, "4.6 (0.89)" should be changed to "–4.6 (0.89)"

Signed and Sealed this  
Nineteenth Day of August, 2025

Coke Morgan Stewart  
*Acting Director of the United States Patent and Trademark Office*